United States Patent [19]

Shilling

[11] Patent Number: 5,115,975
[45] Date of Patent: May 26, 1992

[54] DISPENSER DEVICE AND CARTRIDGE FOR VOLATILE SUBSTANCE WITH RATE CONTROL FOR VOLATILIZATION THEREOF

[76] Inventor: Lynndon Shilling, 630 S. 4th St., No. 36, Ames, Iowa 50010

[21] Appl. No.: 556,476

[22] Filed: Jul. 24, 1990

[51] Int. Cl.$^5$ .......................... B05B 1/24; A61L 9/02
[52] U.S. Cl. ...................... 239/55; 239/57; 239/136
[58] Field of Search ............. 239/53, 55, 56, 57, 239/58, 59, 60, 136, 135

[56] References Cited

U.S. PATENT DOCUMENTS

| | | | |
|---|---|---|---|
| 3,990,848 | 12/1197 | Corris | 239/57 |
| 3,993,444 | 11/1976 | Brown | 239/57 |
| 4,229,415 | 10/1980 | Bryson | 239/57 |
| 4,571,485 | 2/1986 | Spector | 239/136 |
| 4,634,614 | 1/1987 | Holzner | 239/57 |
| 4,695,434 | 9/1987 | Spector | 239/57 |
| 4,753,389 | 6/1988 | Davis | 239/56 |
| 4,809,912 | 3/1989 | Santini | 239/57 |

*Primary Examiner*—Andres Kashnikow
*Assistant Examiner*—Christopher G. Trainer
*Attorney, Agent, or Firm*—Sherman and Shalloway

[57] ABSTRACT

A replaceable cartridge for a diffusion device for a volatilizable substance includes a primary control of diffusion rate of the substance into the surrounding atmosphere. The cartridge includes a base and a cover, and a membrane separating the cartridge into two chambers. The membrane has characteristics for controlling the rate of passage of a vaporized form of the substance from a first chamber, wherein the substance is stored, to a second chamber. A vent structure in the cover provides control over diffusion of the vaporized substance to the atmosphere. The diffusion device may include a heater or other catalyst device for imparting energy to the cartridge, thereby to volatilize the substance, and a timing circuit for control of heater operation. Additionally, the device may include a structure to assist proper placement of the cartridge adjacent the catalyst device by sensing at least a partial insertion of the cartridge and by automatically completing the insertion and positioning process thereof.

17 Claims, 15 Drawing Sheets

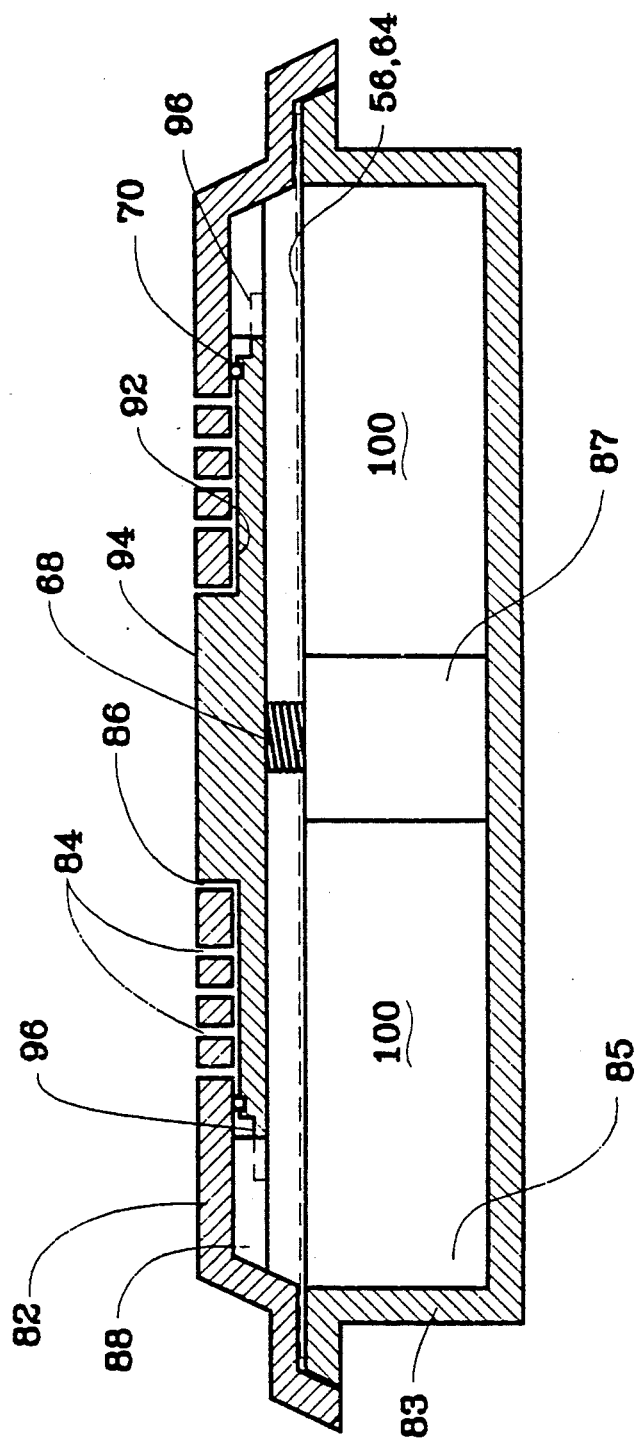

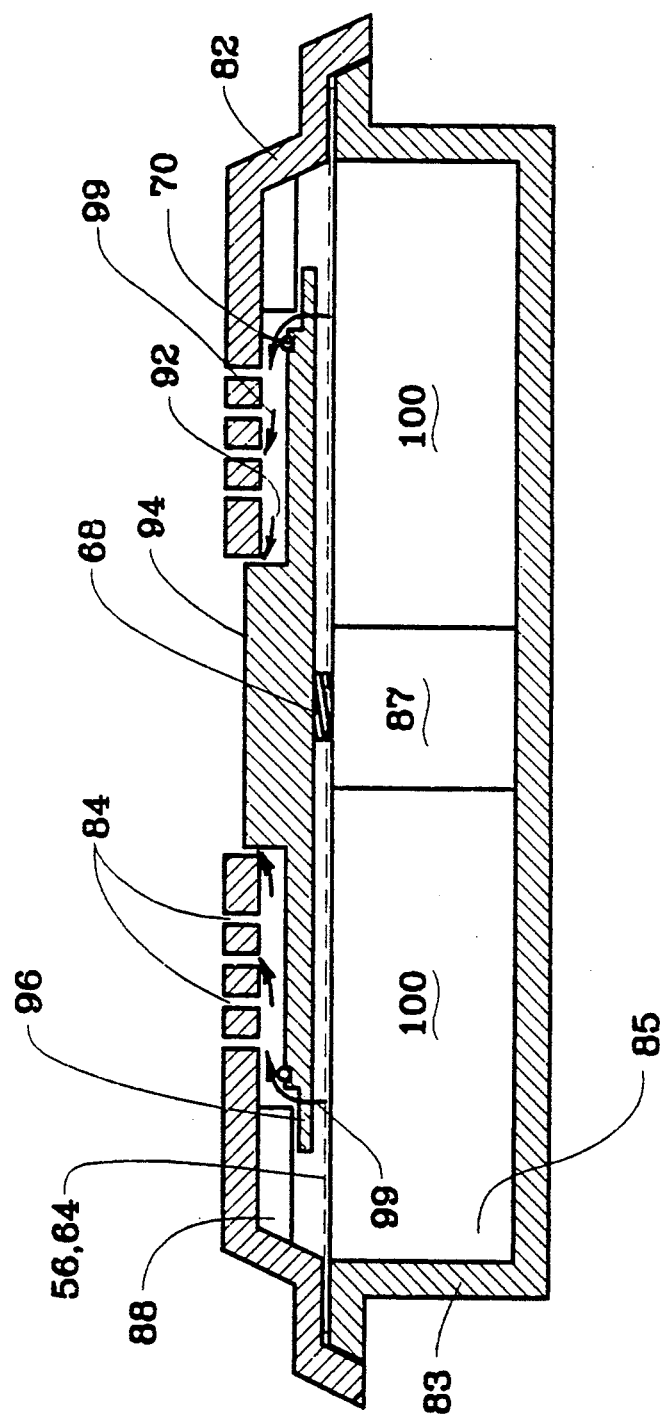

DISPENSER DEVICE AND CARTRIDGE FOR VOLATILE SUBSTANCE WITH RATE CONTROL FOR VOLATILIZATION THEREOF

TECHNICAL FIELD

This invention relates to devices for dispersing volatile substances and more particularly to devices having controlled rates of volatilization for the substance. This invention also relates to a cartridge containing the volatile substance with controllable volatilization and diffusion rate.

BACKGROUND ART

Dispensers for vaporizable and volatilizable substances of many types are known. Such dispensers are used for many types of vaporizable and volatilizable substances, including various scents, disinfectants, medicaments such as decongestants and inhalants, germicidal agents, insecticides, bactericides, fungicides, algicides, anesthetics, cleaning substances, deodorants, reodorants, herbicides, fertilizers, rubefacients, vapor phase corrosion inhibitors, food fragrances, animal repellents, animal attractants, and other substances.

In many of the prior art dispensing devices the substance to be dispersed is absorbed on a pad of absorbent material, impregnated with the substance, and is vaporized from the pad with the aid of a catalytic device such as a heat generator. In a number of such prior art devices there is provided an electric lamp or bulb as a heat generator. In other devices there is provided an electrical heater. The heating is used either to volatilize the substance or to create a pressure differential for forcing heated air through the heated pad, thereby to volatilize the substance absorbed therein.

Other devices are known which include a vent structure to permit vaporization of the substance from the pad, or from a reservoir of liquid material, into the surrounding ambient atmosphere upon opening of the vent. Still other devices are available which provide disposable cartridges for a single use.

However, prior art does not disclose devices in which the vaporizable substance is dispersed at a rate which may be selected by the user, whether by selective opening of passageways within a replaceable cartridge or by electronic control vent means and/or of a heating circuit within the device receiving the disposable cartridge.

There is thus a need in the art for cartridges having adjustable controls for varying the rate of vaporization of a volatilizable substance enclosed therein. There is also a need in the prior art for disposable cartridges having a storage arrangement therein for a volatilizable substance and for effecting a precise rate of volatilization thereof.

There is also a need in the art for dispensing devices for vaporizable substances included in disposable cartridges inserted therein, the cartridges having structural facilities for controlling the rate of volatilization of the enclosed substance, and wherein the device includes electronic controls for adjustably controlling the release of volatilized substance from the cartridge, thus controlling the timing of vaporization and dispersing of the substance.

There is yet a further need in the art for vaporizing devices including therein structure for facilitating the insertion of disposable cartridges, thus to assure proper alignment of the same within the device.

DISCLOSURE OF INVENTION

It is accordingly an object of the present invention to overcome the deficiencies of the prior art and to provide an improved apparatus for controllably diffusing a volatilizable substance in an ambient atmosphere.

It is a more particular object of the invention to provide a replaceable cartridge containing a volatilizable substance and structure for controlling the rate of diffusion of the substance into the atmosphere.

Still another object of the invention is to provide a cartridge for a volatilizable substance having a membrane separating the interior of the cartridge into first and second chambers, wherein the characteristics of the membrane are selected to provide a desired rate of passage of a vapor form of the substance from the first to the second chamber and thus to the ambient atmosphere.

It is an additional object of the invention to provide a replaceable cartridge for a volatilizable substance including a cover cooperating with a base for enclosing the membrane in the cartridge wherein the cover includes a control structure for further controlling release of the volatilizable substance into the atmosphere.

It is still another object of the invention to provide a replaceable cartridge for a volatilizable substance in which a cover cooperates with a base to form a chamber in which there is provided a membrane having predetermined characteristics to establish a primary control of diffusion of the substance into the atmosphere, and to provide a secondary control of diffusion of the substance by providing the cover with a vent structure for venting the vaporized substance from the cartridge to the ambient atmosphere.

It is yet another object of the invention to provide a replaceable cartridge for a volatilizable substance, including a membrane for establishing a primary diffusion control of a rate of diffusion of the substance to the atmosphere and a vent structure including a vent seal for releasably sealing an opening in the cartridge to establish a secondary diffusion control of passage of the vaporized substance from the cartridge to the ambient atmosphere.

It is an additional object of the invention to provide an improved diffusion device for diffusion of a volatilizable substance into the ambient atmosphere, including a replaceable cartridge containing the substance and establishing control over a diffusion rate thereof, a heater or other catalyst for volatilization of the substance within the cartridge, and a timing control device for controlling timing of release of the vapor form of the volatile substance from the cartridge and device.

It is a further object of the invention to provide an improved diffusion device for diffusion of a volatilizable substance into the ambient atmosphere, including a replaceable cartridge containing the substance and apparatus for sensing at least partial insertion of the cartridge into the device, thereby to activate circuitry for heating the cartridge and for positioning the cartridge to receive heat from a heater in the device.

In accordance with the above objects of the invention, there is accordingly provided an improved apparatus for diffusion of a vaporizable substance into an ambient atmosphere. More particularly, in accordance with one aspect of the invention there is provided a replaceable cartridge containing a volatilizable substance for diffusing into an ambient atmosphere. The cartridge structure advantageously provides control of diffusion of the substance, and includes a base, and a membrane cooperating with the base to form a first chamber for containing the substance for volatilization. In the cartridge there is also provided a cover cooperating with the base for enclosing the membrane in the cartridge. A second chamber is formed between the cover and the membrane, for the vaporized substance. The cover includes a vent structure for venting the vaporized substance from the second chamber to the ambient atmosphere, and a vent seal is provided for releasably sealing the vent structure to permit controlled passage of the vaporized substance from the cartridge to the ambient atmosphere.

In addition to the membrane, there is preferably included a support member therefor, the support member including a port structure for passage of the vaporized substance from the first chamber to the second chamber. Preferably, the membrane has predetermined characteristics for controlling a dispersal rate for a vaporized form of the substance. The membrane may have a porous structure. The pores of the porous structure may be substantially uniform in size or may be non-uniformly distributed, pores of a larger diameter being distributed in the membrane closer to the second chamber and pores of a smaller diameter being distributed in the membrane closer to the first chamber.

In one embodiment of the invention, the vent seal includes a diaphragm for opening and closing an opening in the vent structure, a sealing ring surrounding the diaphragm for sealing the closed vent structure, a spring for biasing the diaphragm against the cover, and, optionally, a support chamber for supporting the spring. The support chamber, when present, may include a cylindrical chamber in the first chamber of the cartridge, and may further include an opening in the membrane for one or both of the spring and the cylindrical chamber.

In accordance with another embodiment of the invention, the vent seal may include a cylindrical chamber in the first chamber of the cartridge, a biasing spring within the cylindrical chamber, and a rotatable cover. Preferably, the rotatable cover includes a cover for opening and closing the opening in the vent structure and a keyed shaft therefor, while the cylindrical chamber includes a circumferential slot engaging a key of the keyed shaft. Thus, when the shaft is longitudinally displaced in the cylindrical chamber against biasing force exerted by the biasing spring, the cover rotates in order to provide controllable opening and closing of the opening in the vent structure.

In accordance with still another embodiment of the invention, a push-button, or other compression device, may be included within the cartridge casing for displacing the diaphragm or the rotatable cover against the bias exerted by the spring to open and close the opening in the vent structure, thereby further controlling passage of the vaporized substance from the cartridge to the ambient atmosphere.

The inventive diffusing apparatus preferably includes a catalyst device for emitting energy to release the substance from a carrier therefor, and a control circuit for controlling the opening-closing of the vent seal of the cartridge inserted into the diffusing apparatus.

The catalyst device may include a heater for heating the cartridge, an ultrasonic device or other energy emitting device, and the control circuit includes timing circuitry for controlling timing of opening and closing of the vent seal to control the release of volatilized substance from the cartridge and, hence from the diffusion device. The control circuit includes a vent control arrangement for engaging the vent seal of the cartridge and for controlling operation thereof, thereby providing control of passage of the vaporized substance from the cartridge to the ambient atmosphere. Additionally, the control circuit of the diffusion device may include a displacing apparatus for sensing partial insertion of the cartridge into a slot and for positioning the cartridge to receive energy from the heater (or other energy emitting device) to effect volatilization of the substance.

The foregoing and other objects, features and advantages of the present invention will become readily apparent to those skilled in the art from the following description and drawings, wherein there is shown and described preferred embodiments of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWING

In accordance with the above described objects and features of the invention, and preferred embodiments thereof are shown in the accompanying drawings, wherein:

FIG. 9 illustrates an alternate embodiment of a vent sealing structure for the inventive cartridge;

FIG. 16 is a section view of the cartridge shown in FIG. 14 showing the components thereof assembled therein with the push-button vent sealing device in the "closed" position;

FIG. 17 is a section view similar to FIG. 16 but with the push-button sealing device in the "open" position.

BEST MODE FOR CARRYING OUT THE INVENTION

Figure 1:
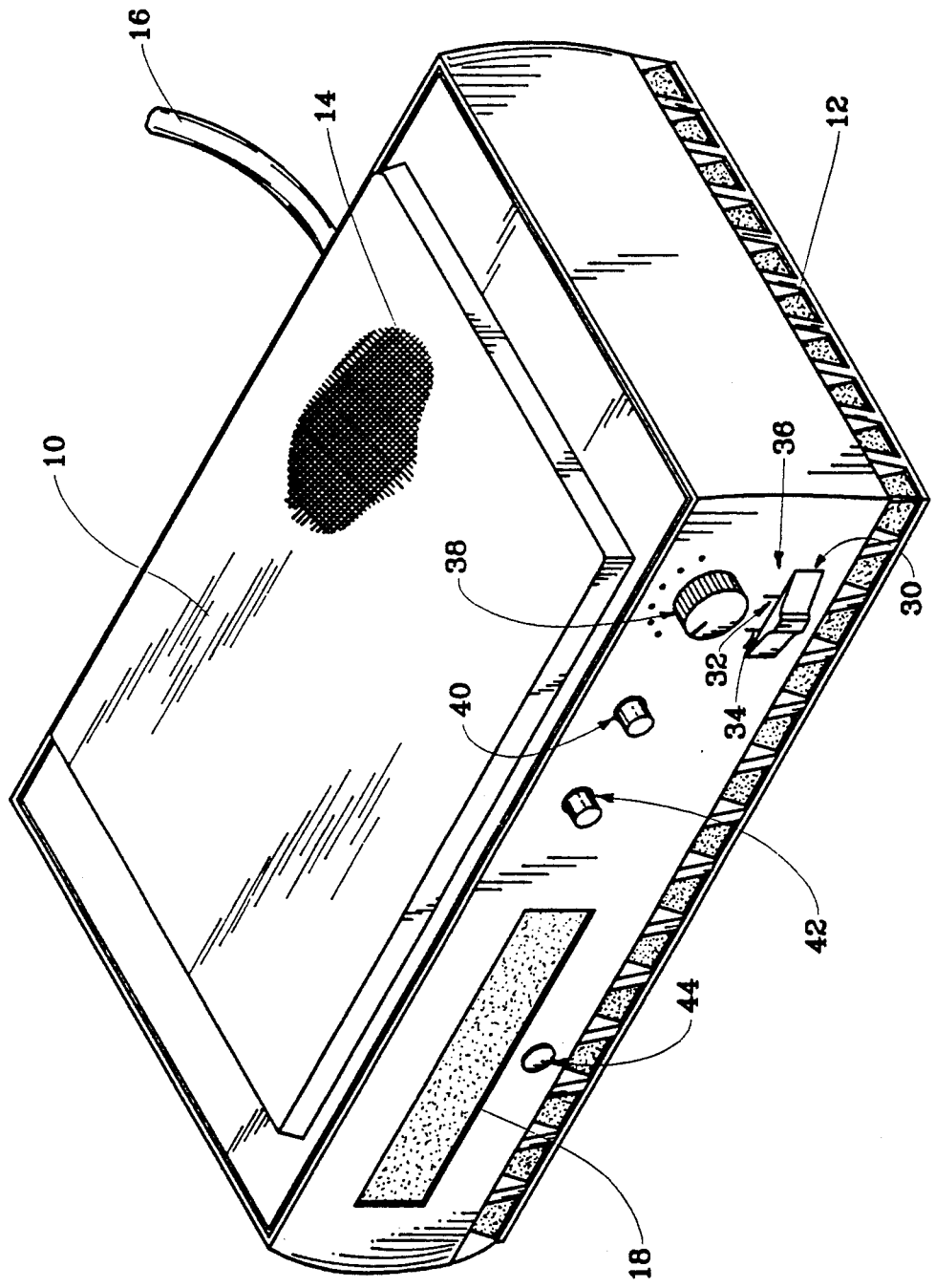
FIG. 1 shows a perspective view of a diffusion device incorporating concepts of the invention.

Referring now to the embodiment of the invention illustrated in FIG. 1, there is illustrated a diffusion control device including the various aspects of the invention. The device is generally shown at 10, and includes a replaceable cartridge (see e.g. FIG. 4 and FIG. 14) containing the vaporizable substance. To aid in distributing the vaporized substance, there are provided a bottom (inlet) port 12 and an upper (outlet) port 14 (partially shown) for discharging the vaporized substance.

Electric power is provided to the device by means of an electrical cord 16, although it is recognized that the device may be powered by D.C. current, e.g. internal or external batteries, by solar power, or by other means.

Figure 4:
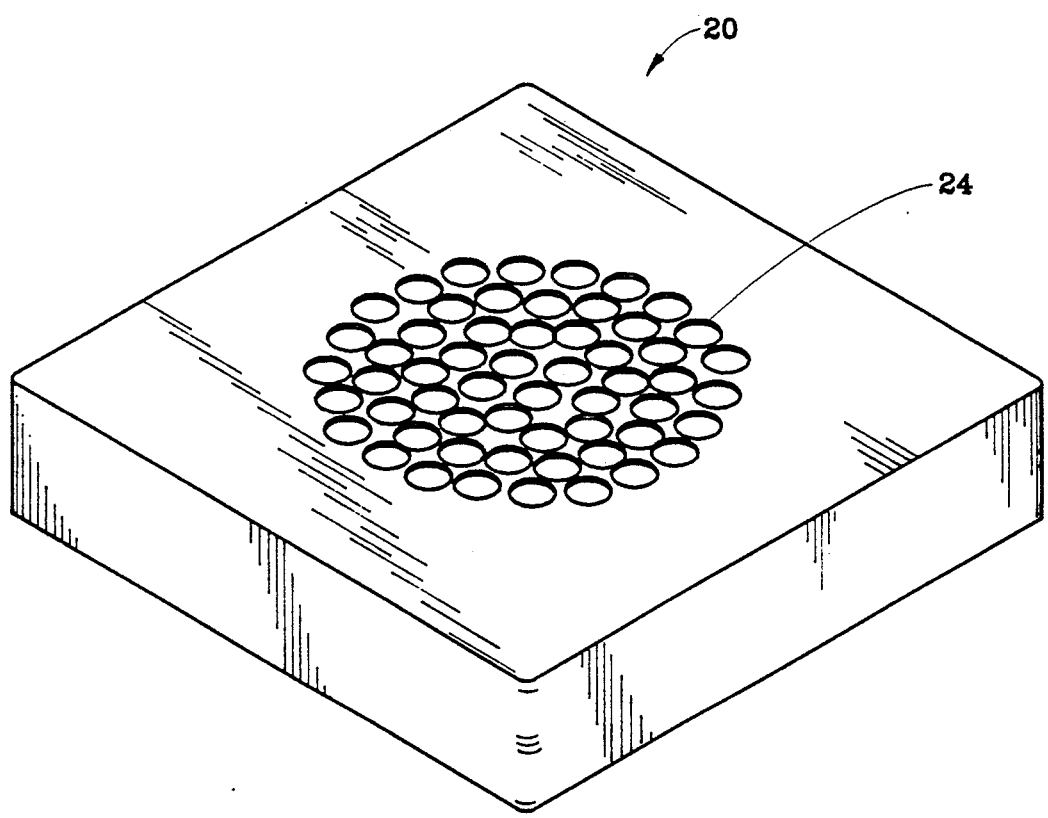
FIG. 4 is a perspective view of a cartridge according to the invention.

A slot 18 is provided in the front face of the device for receiving a cartridge of the type illustrated in FIG. 4 and described in detail in connection therewith. Although a rectangular slot is shown, it will be appreciated that any shape may be used for the slot and the cartridge received thereby, such as the cylindrical cartridge 80 shown in FIG. 14. However, it should also be recognized that different slot shapes may be provided in different models of the device and to cartridges containing different volatilization substances in order to limit the types of cartridges which may be accepted thereby, thus providing additional control on proper use of the devices.

The inventive device may include a switch 22 (shown in FIGS. 2-3) for sensing insertion of a cartridge 20 (FIG. 4) into slot 18. The switch is used to activate a catalyst device, such as an electrical heater, and may also be used to activate an optional cartridge positioning device 21.

Figure 7:
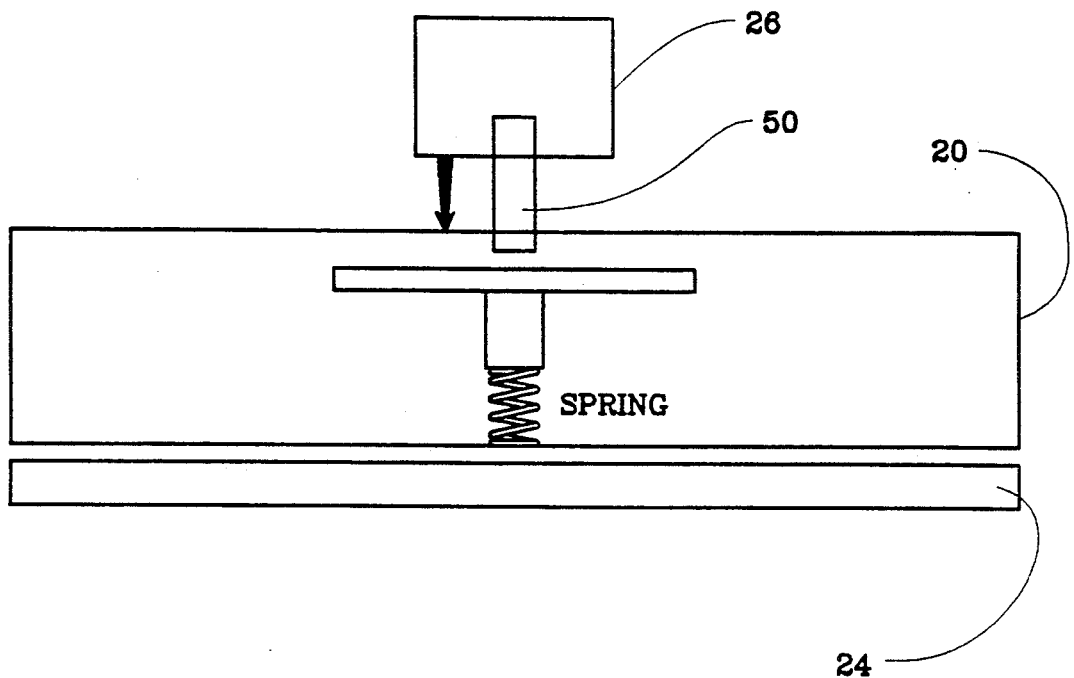
FIG. 7 is a section view of the cartridge of FIG. 4 as engaged by a vent controller of the device of FIG. 1.
Figure 18:
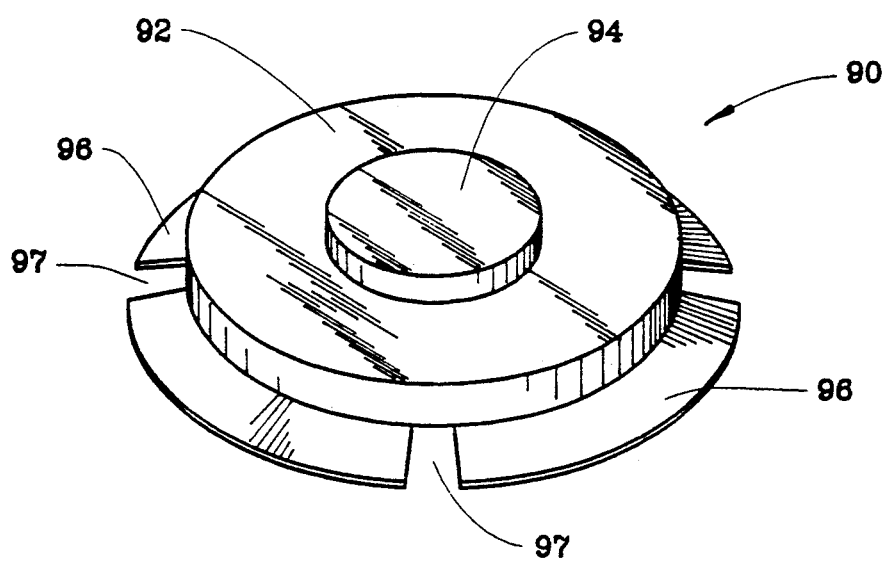
FIG. 18 is a perspective view of a push button vent seal mechanism as shown in FIGS. 16 and 17 for controlling release of volatilized substance through the vents of the cartridge shown in FIG. 14.
Figure 13A:
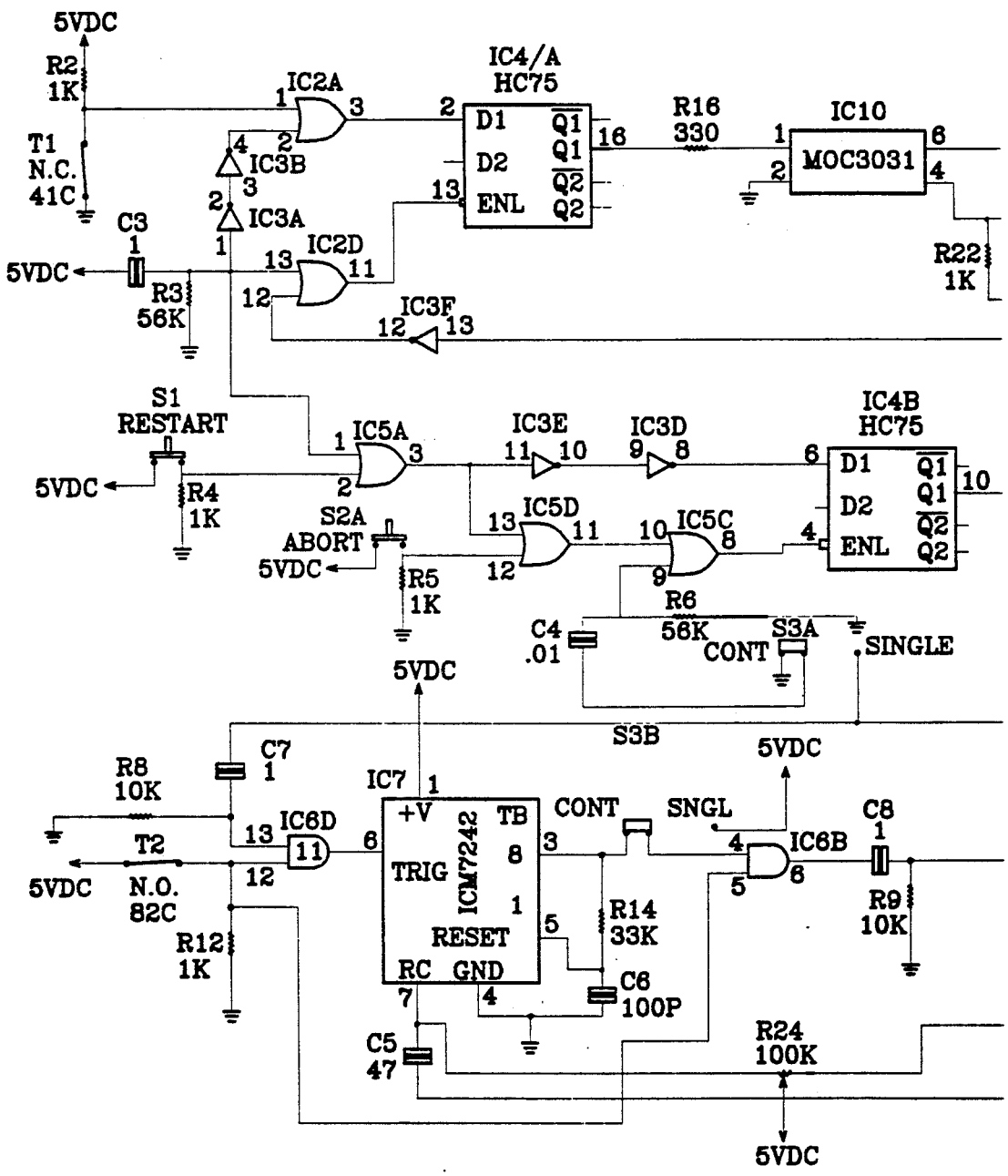
FIGS. 13A and B is an electrical schematic diagram illustrating various electrical components used in a control circuit of the device of FIG. 1.
Figure 13B:
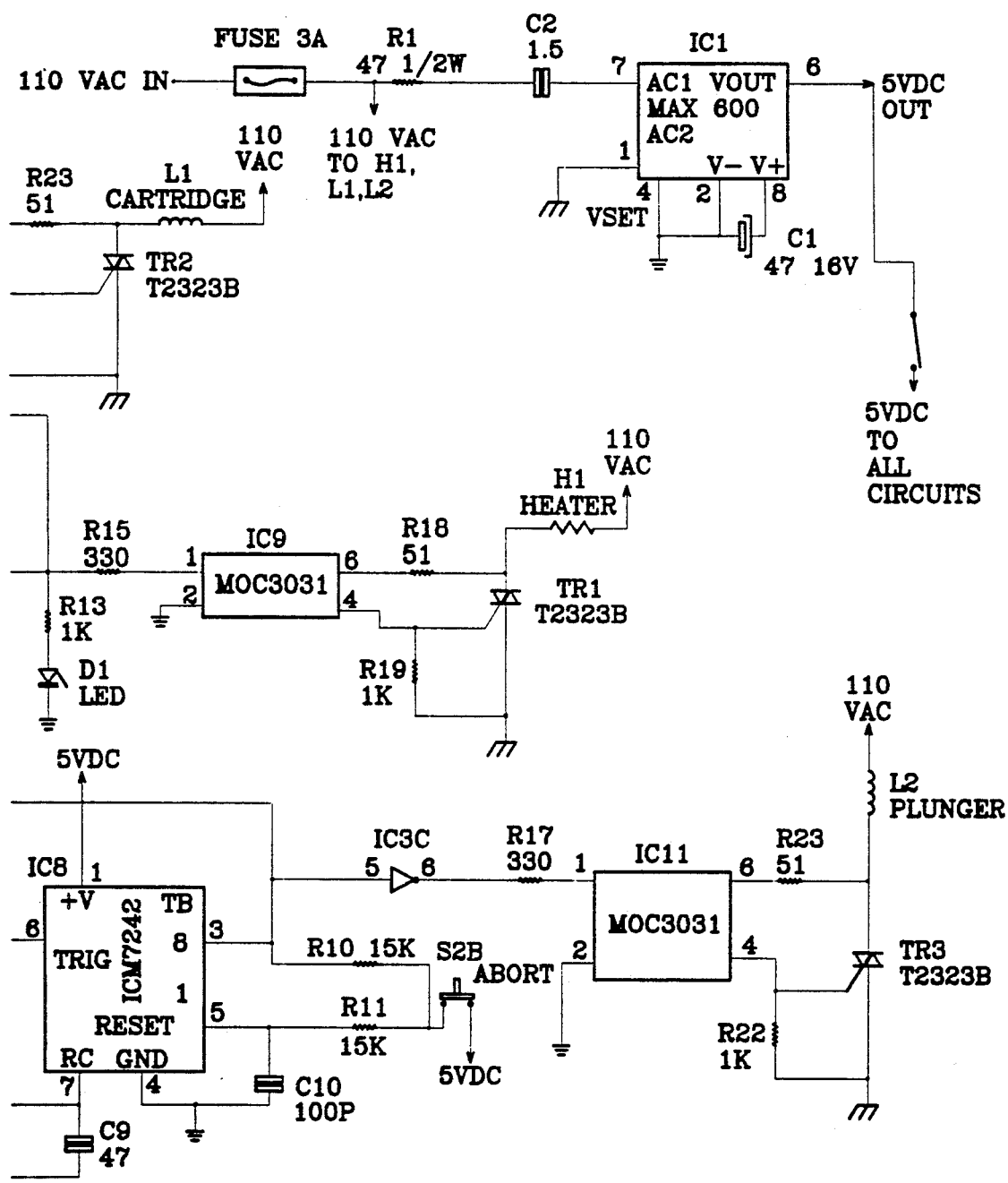

The heater may be a hot plate 24 shown in FIG. 7, or may be any electrical heater as schematically shown in FIG. 13. The cartridge positioning device 21 may be provided in the form of solenoids or motors (described in connection with FIG. 13), activated by sensor switch 22 upon fully inserting the cartridge in a position properly aligned with the heater. Whether or not the device includes a positioning device, there are provided guides 28 for aiding in insertion of the cartridge.

Moreover, the switch may be used to activate a vent seal activating solenoid 26 (FIGS. 2, 7) for displacing a vent seal mechanism in cartridge 20, thereby to open vents therein to permit the vaporized substance to diffuse into the ambient temperature through the top outlet diffusion port 14 of the device.

Figure 2:
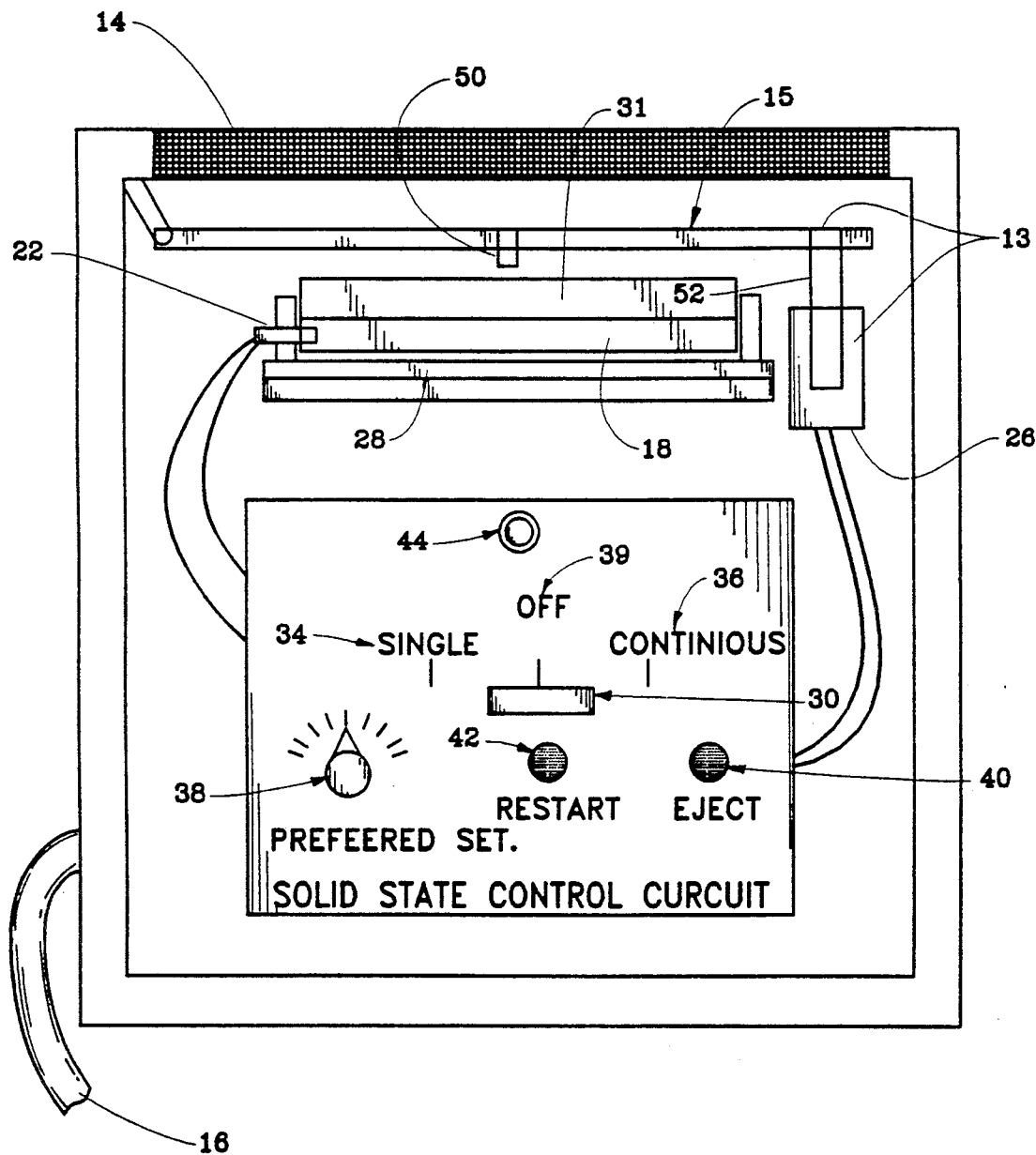
FIG. 2 is a view of a device similar to FIG. 1 and illustrating an internal cartridge positioning apparatus therein.
Figure 3:
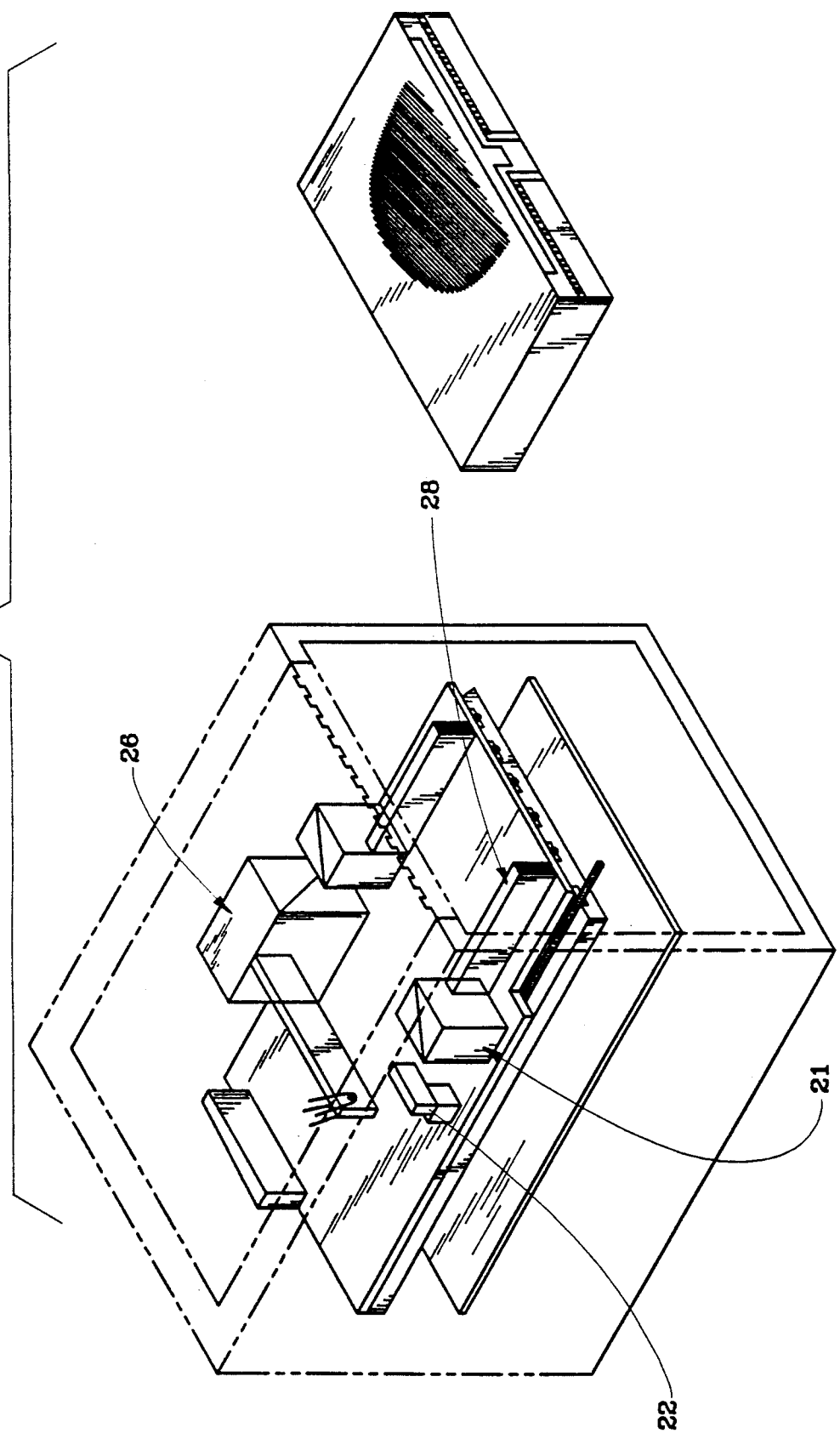
FIG. 3 is a perspective view showing further details of the cartridge positioning apparatus of FIG. 2.

As seen in FIGS. 1, 2, a number of control switches are provided to permit the user to exercise control over the rate and timing of diffusion of the vaporized substance into the atmosphere. Thus, there is provided a three pole main control slide switch 30 for turning the device off or on, by selecting among switch positions 32, 34 or 36. Switch position 32 selects the OFF state for the device, in which power is removed from the electrical control circuits of the device. Of course, a push-button (FIG. 17) may be provided on the cartridge to permit manual operation of the vent seal structure thereof, thereby to allow the user to manually open and close the cartridge vents independently of the energization of the device 10 or solenoid 26.

Such a push-button may have a single setting, as in the embodiment shown in FIGS. 14 to 17, to provide a fully opened cartridge vent or vents, or may be rotatable (e.g. in conjunction with the cartridge structure of FIG. 9) or may have other provisions for multiple settings, thereby to provide control over the rate of release of the vaporized substance into the ambient atmosphere. Similar variable control may be provided by the circuitry of FIG. 13 over operation of solenoid 26.

As will be appreciated by those of skill in the electrical arts, the circuit of FIG. 13 causes the solenoid 26 to remain de-energized if slide switch 30 is in the OFF position 32. When placed in either of the positions 34 or 36, slide switch 30 causes energization of solenoid 26 thereby to open the vents of cartridge 20. In the SINGLE BURST position 34 the circuit of FIG. 13 causes a single burst of the substance to be diffused, for a time period determined in accordance with a setting of a duration control switch 38. Thereafter, after a predetermined delay period, the cartridge may be retained in the device or may be discharged by the positioning device 21. Towards that end, the circuit of FIG. 13 may be designed either to provide automatic discharge of the cartridge following the burst duration, or to retain the cartridge pending activation of a separate eject switch 40.

If it is desired to obtain another burst of the substance within the cartridge, a restart switch 42 may be operated during the aforementioned delay period prior to discharge of the cartridge. The circuitry of FIG. 13, in response to activation of switch 42, then again activates the single burst function.

Alternatively, the switch 30 may be positioned to continuous operation position 36, causing the control circuitry of FIG. 13 to provide continuous heating of the substance, by providing separate bursts (open vent) of predetermined durations, as established by setting switch 38, and separated by predetermined periods (closed vent) established by switch 38 or by a separate switch. In that regard, as known in the art the switch 38 may establish the duration of the burst periods (open vent) or may establish both a duty cycle of operation and the burst durations, in accordance with well known principles for connection and operation of the timing circuits of FIG. 13.

Thus, once switch 22 senses insertion of the cartridge, hot plate 24 is activated and an indicator, such as LED 44, is activated to alert the user to the fact that the heater is operated.

A thermostatic control, including a pair of thermostats 46 and 48 shown in FIG. 13, is used to provide thermal stability to operation of the inventive device. Thus, thermostat 46 (normally closed for temperatures below 41° C.) opens at a predetermined temperature, illustratively selected at 41° C., to initiate the intermittent operation of solenoid 26 to open and close the cover vents of cartridge 20 in accordance with a predetermined duty cycle.

When operating in the continuous duty mode of operation, eject switch 40 may be used to interrupt operation by turning off the heater and, after a short delay, causing the control circuit to eject the cartridge. Alternatively, operation may be interrupted by placing switch 30 in the OFF position (32), thereby to shut down all power supply to the device and retaining the cartridge in place, in a vent closed position.

As hereinabove noted, the cartridge vent opening mechanism may include solenoid 26. Although in the embodiment of FIG. 7 the solenoid is directly connected to a member 50 for opening and closing the vents, the opening member 50 may, instead, be operated via a linkage 52 which is activated by solenoid 26, as shown in the embodiment of FIG. 2. The solenoid 26 may, of course, be replaced by a motor or other device and linkage mechanism may include levers, bars or other members, for pushing or pulling a spring loaded vent seal of the cartridge, as shown in FIG. 5.

Figure 5:
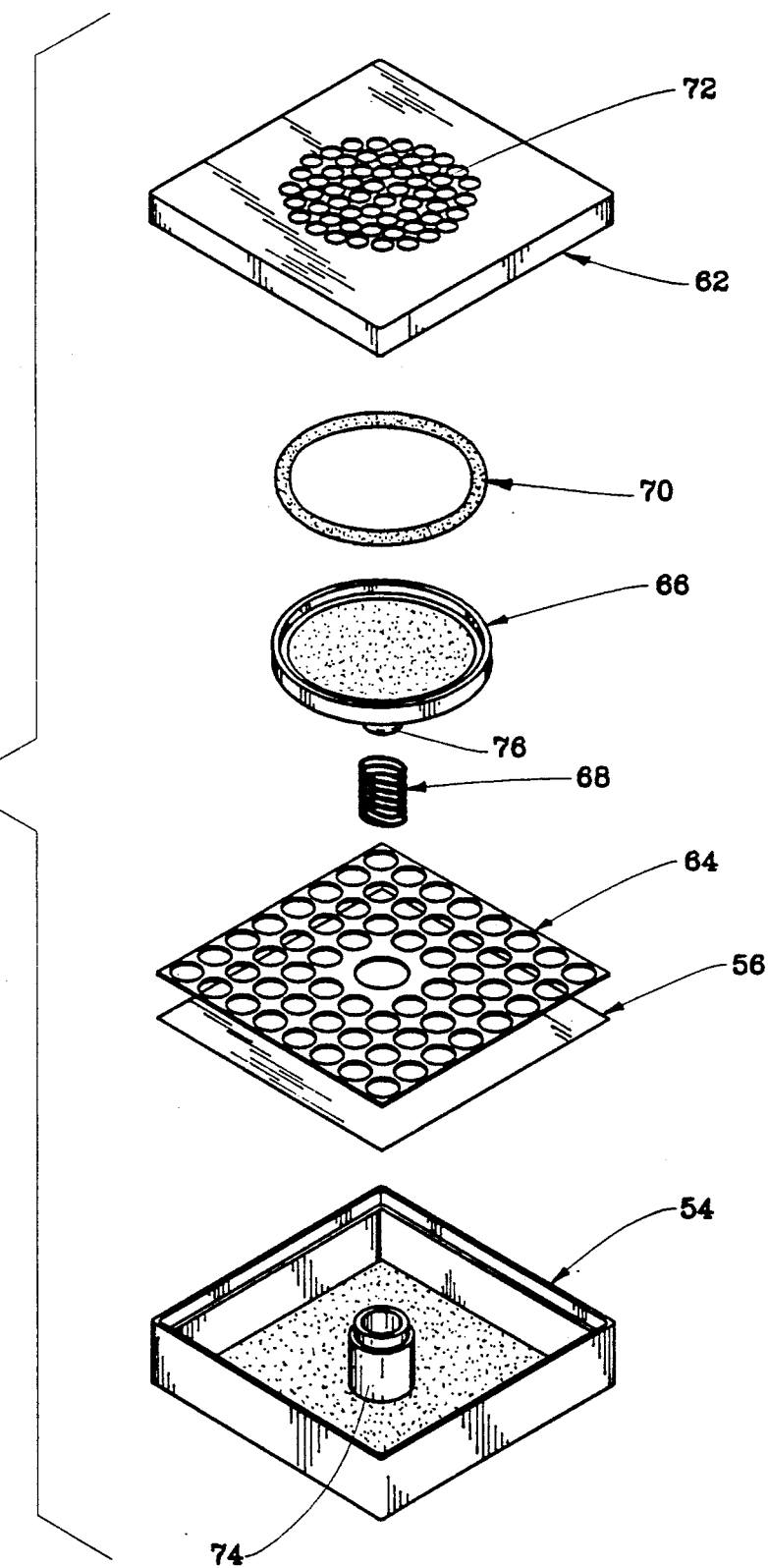
FIG. 5 is an exploded view showing details of the cartridge of FIG. 4.
Figure 6:
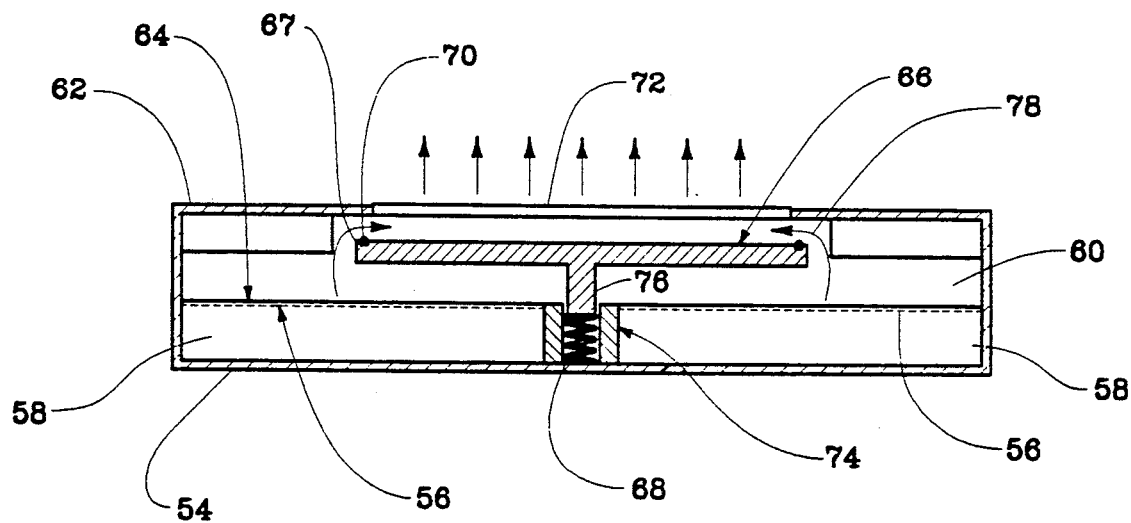
FIG. 6 is a section view of the cartridge of FIG. 4 showing the components of FIG. 5 as assembled therein with the vent seal in the "open" position.

Referring now to FIGS. 5 and 6 there is shown in detail the construction of a cartridge in accordance with the invention. Specifically, a base member 54 forms the bottom of the cartridge. A control membrane 56 is provided to control the rate of dispersal of the substance from a lower chamber 58, formed between base 54 and membrane 56, to an upper made of a thermally conductive material, resistant to the heat level required for the volatile substance, both immediately upon contact and as the mass evaporates. Moreover, the material is chemically resistant to the volatile substance at room temperature, as well as at the initially required heat level and at the increased temperatures occurring as the mass of the substance evaporates. Thermal plastics, which may include fillers such as glass, talc, aluminum or the like, may be used. Alternatively, materials such as cast aluminum, die punched aluminum, ceramics, glass or other thermally conductive materials may be used.

A support member 64 provides support for membrane 56 and prevents the membrane from becoming entrapped in a seal between a diaphragm 66 and cover 62. The support member may be formed from an apertured or perforated metal, e.g. aluminum, foil, film or sheet. Plastic netting material having a softening temperature above the maximum temperature encountered during use can also be used as the support member. For example, open mesh netting made from Tyvek (a trademark of E.I. du Pont) is a light weight structurally strong, high melting point material which has been successfully used as a membrane support material.

A spring 68 biases diaphragm 66 against cover 62 and an O-ring 70 establishes an appropriate seal between the diaphragm and the cover, thus sealing vent openings 72 provided in the cover. As shown in FIGS. 5 and 6, O-ring 70 fits securely within groove 67 of diaphragm 66. Alternatively means (not shown) can be provided in the underside of cover 62 for securely holding the O-ring seal and groove 67 may then be omitted, i.e. diaphragm 66 may then have a flat upper surface for engagement with the O-ring secured to cover 62. A cylindrical spring support chamber 74 is provided for retaining the spring 68. The diaphragm may include a shaft 76 which is surrounded by the spring 68 so that the spring exerts a biasing force directly on the diaphragm and any supporting structure therefor. Alternatively, the shaft 76 may rest on the spring 68, as shown in FIG. 6. In either structure, support 74 provides a passageway for retaining shaft 76 while the diaphragm 66 travels to open and close the openings 72 of cover 62. If spring 68 surrounds shaft 76, however, it will be appreciated that shaft 76 may not necessarily be required to be constrained to travel within the cylindrical support chamber 74.

The O-ring 70 and spring 68 are selected from materials capable of withstanding the temperature requirements of the specific substance being vaporized. Additionally, the O-ring 70 is chemically compatible with the substance being vaporized, so that no chemical interaction takes place therewith. It will be appreciated that expansion of the O-ring is considered in selecting its component material, to assure that variations in the diameter thereof with changing temperatures and spring pressure do not result in breaking of the seal with the cover.

It will also be appreciated that in place of the O-ring seal, other means for effectively blocking access of vaporized substance to the vent openings 72 can be provided in association with the vent seal mechanism. For example, the upper surface of diaphragm 66 may be provided with a soft, resilient cover layer which effectively completely covers the vent openings when diaphragm 66 is held in its uppermost position (shown by dotted lines in FIG. 6) by the upward force of spring 68.

Referring once again to FIG. 6, the internal structure of the cartridge is shown with the diaphragm 66 displaced to open an internal vent 78 thereby to permit the vaporized substance to exit chamber 60 via vent openings 72, as illustrated by the vertical arrows in the figure. The flow of the substance is primarily controlled by the structure of membrane 56 and secondarily by the degree of opening of internal vent 78 in the cartridge. It will be appreciated that chamber 60 is the container for the vaporized volatile substance. Thus, whether the vent seal arrangement is open or closed, the highest concentration of the vaporized substance is found therein.

The primary control over the amount of vapor exiting through vent openings 72 is provided by membrane 56. Where a microporous film is used, condensation of the vapor is inevitable and is used by the inventive structure to provide the desired control. Particularly, referring to the representative illustrative materials which may be used for the membrane, shown in FIGS. 8a-8c, flow back of the condensed material through the membrane into the lower chamber may be used advantageously. Thus, appropriate selection of the material used for the membrane provides advantages beyond those offered by the multichamber structure and displaceable vent seal hereinabove described.

The rate of transport of the vaporized substance through the film is an initial factor considered in selecting the appropriate material. This factor, called the moisture transmission rate and measured in grams per square meter per 24 hours, does not require that a porous material be used.

Figure 8A:
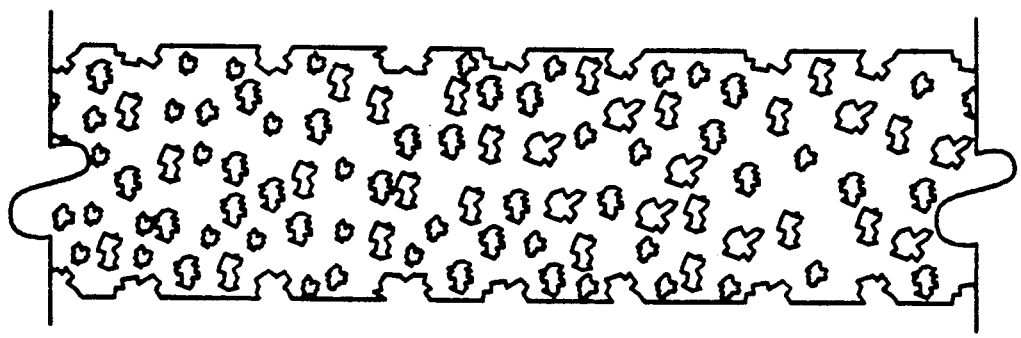
FIGS. 8a, 8b and 8c show samples of a membrane used in the cartridge according to the invention.

The sample of material shown in FIG. 8a has a nonuniform distribution of pores in the membrane. Therein, pores of larger sizes are distributed more closely to the surface of the membrane adjacent the upper chamber 60, while pores of smaller sizes are distributed more closely to the surface of the membrane adjacent the lower chamber 58. Such an arrangement provides enhanced leak-proofness, together with vapor transmission and the previously mentioned flow-back of condensate to lower chamber 58.

Figure 8B:
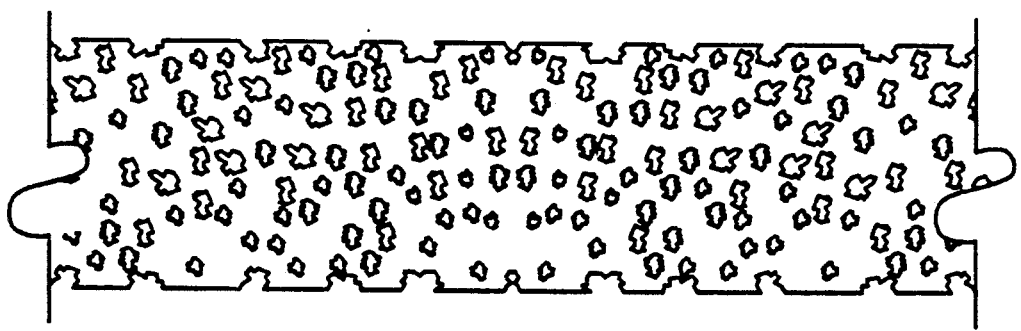
Figure 8C:
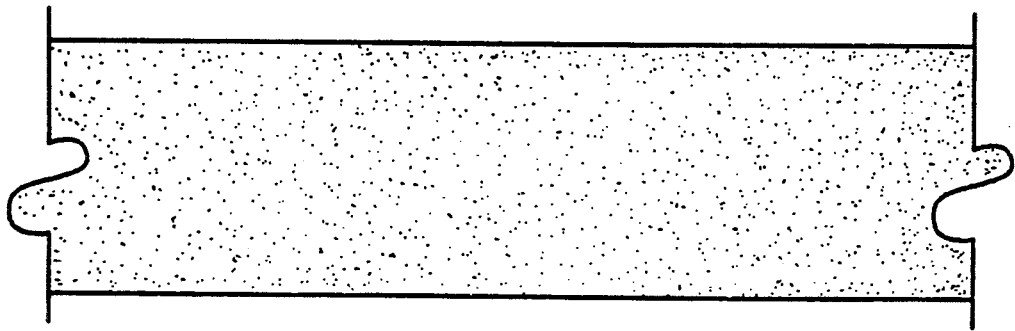
Figure 4:
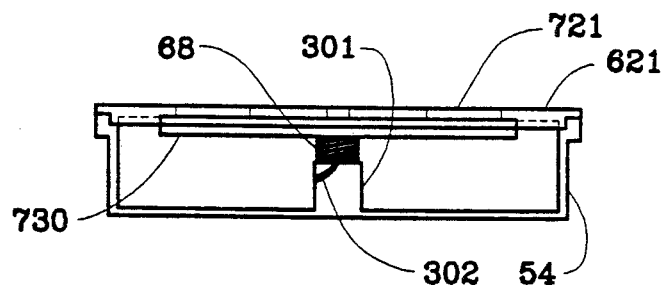

The sample of material shown in FIG. 8b has a uniform pore size in the membrane, which restricts flow-back transmission still further. In the sample of FIG. 8b any flow-back typically occurs while the cartridge is cooling. The sample shown in FIG. 8c illustrates that while a non-porous film is used, the volatile material may still travel through the polymer structure by connecting with the oils, elements, and inorganic compounds used in the plastic industry. Many films have low vapor barriers to many fragrance and other volatilizable materials.

The thickness of all materials used for the membrane provides a standard for adjustment of the vapor transport rate. In view of the relatively thin nature of the membrane, for example, on the order of from about $1 \times 10^{-5}$ to $1 \times 10^{-1}$ inch, preferably from about $5 \times 10^{-5}$ to $5 \times 10^{-2}$ inch, support member 64 (in the form of screening, open mesh, netting, perforated film, etc.) is provided for membrane 56, including therein openings, apertures, or perforations to provide ports for avoiding blockage of the vapor in transit from the lower chamber 60 to the upper chamber 58. The support member will also be made as thin as possible, for example, from about $1 \times 10^{-3}$ to $2 \times 10^{-1}$ inch, preferably about $5 \times 10^{-3}$ to $5 \times 10^{-2}$ inch. The structure and positioning of support member 64 keeps membrane 56 from expanding upwardly, and lodging in the vent seal, as heat is applied to the lower chamber 60 and pressure of the vapor therein is increased. As is known in the art, such increased pressure enhances the volatilization process.

Hermetic seals, e.g. heat seal, fusion bonding, sonic welding, etc., are provided for the membrane 56 at base 54 and at the optional cylindrical spring support chamber 74. As hereinabove noted, the support chamber 74 also provides a guide for travel of the diaphragm shaft 76. However, the guide may be designed into the cover 62, so that the cylindrical spring support 74 would function strictly as a pedestal for the spring. Also, as described above in connection with FIG. 16, support chamber 74, as well as shaft 76, may be omitted and spring 68 may be welded, glued, or otherwise affixed to the underside of diaphragm 66.

In addition to the hermetic seal between the membrane (or membrane and support) and the base of the cartridge, an air tight seal is also provided between the cartridge base and cartridge cover. Suitable seals can be obtained with suitable adhesives which can withstand the normal operating temperatures of the device and the expansion-contraction cycles coinciding with the usual heating-cooling cycles. Preferably, however, the cover and base, after loading of the vaporizable substance in the appropriate chamber or chambers provided therefor, and after securing the membrane to the base, and inserting the particular vent seal assembly, are sonically welded to each other by procedures well known in the art.

As previously noted, the membrane 56 provides control of dispersal of the vaporized substance. Such control is attained by restricting the vapor transmission by a certain percentage, which varies from material to material. Polyolefins, e.g. polypropylene, have advantageously been used as the membrane. Of course, any other material which will be inert to the vaporized substance, able to withstand the operating temperatures and have sufficient mechanical strength can be used in the invention. Vapor transmission tests have been conducted for a specific fragrance oil, and similar tests may be used to identify particular materials for use as membranes in cartridges for other substances.

In one experiment, two small jars were filled with 50 ml of oil No. 109-693, known as Revitalize. The initial weights of the two jars were 52.1887 and 52.9065 grams, respectively. The first jar was covered with a membrane of material known as FS-1, while the second jar was left uncovered, and both jars were placed on a hot plate heated to 100° C. The jars were weighed again after 24 hours and the respective weights were 51.2672 and 49.4040 grams. The total material lost was thus 0.9215 and 3.5025 grams, respectively from the two jars, so that the membrane created a 74% barrier to the fragrance oil as compared with the uncovered jar.

In a second experiment, two beakers were placed on a hot plate heated to 105° C., the first beaker being covered with a membrane and the second uncovered. The two beakers weighed 46.4260 and 49.5500 grams, respectively, and samples of 17.0775 and 17.7319 grams of paraffin were used. After 48 hours on the hot plate, the beakers lost 0.0651 and 2.2499 grams, respectively, showing that only $0.0651/2.2499 = 2.8934\%$ of the uncovered sample loss was experienced in the covered beaker, or that FS-1 with support causes a 97% restriction on vapor transmission of paraffin.

Similar tests may be performed on other membrane materials and substances to be volatilized in order to select appropriate membranes for control of the rate of dispersal of the vaporized substance into the atmosphere.

Generally, good results will be obtained, depending on the intended area (volume) of application, the nature and volatility of the volatile substance, etc., with membrane having water vapor transmission rates of at least about 800 $g/m^2 0.24$ hr, preferably at least about 1000 $g/m^2 0.24$ hr. Also, for a wide range of volatile substances effective control of diffusion rates can be obtained with membranes in the above range of thickness and with porosities in the range of from about 50% to about 90%, preferably 65% to 85%, and pore sizes ranging from about 0.08 to about 3 microns, preferably from about 0.15 to about 2.2 microns, especially from about 0.3 to about 1.6 microns.

While the above tests were carried out using pure essential oils or paraffin as the vaporizable substance, it will be appreciated by those of skill in the art that a broad range of volatile substance, including, for example, air-improving agents (e.g. air sanitation, air freshening, air medicating, air deodorizing, perfumes), fungicides, herbicides, animal repellants and attractants, veterinary medicines, vapor phase corrosion inhibitors, food fragrances, and the like, can be dispensed using the cartridge and dispenser device of the invention. Furthermore, the volatile substance can be used in the pure liquid or solid form as a component of a liquid, gel or solid formulation with suitable carriers, thickeners, gellants, diluents, and the like, as well known in the art.

Figure 10:
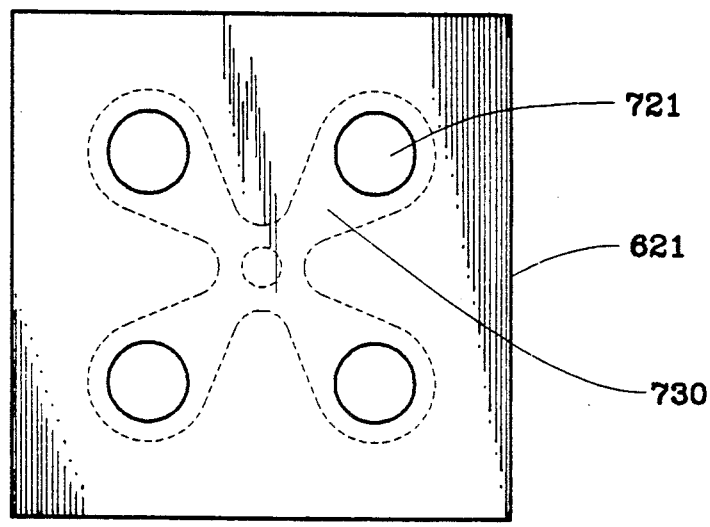
FIG. 10 illustrates the vent sealing structure of FIG. 9 in a closed position.
Figure 11:
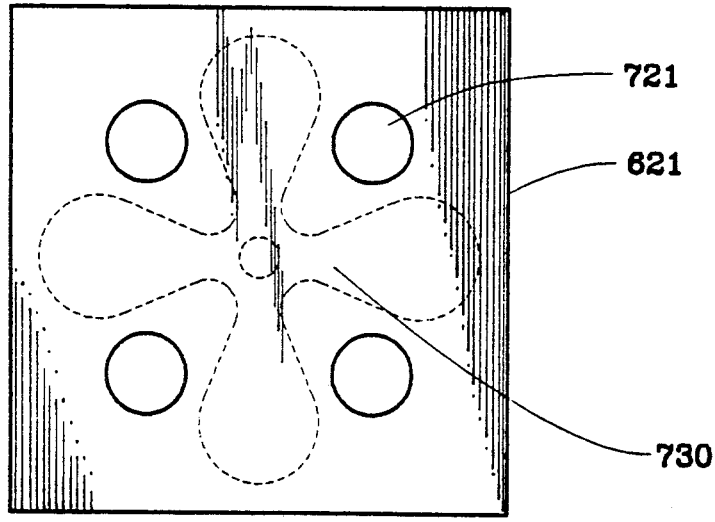
FIG. 11 illustrates the vent sealing structure of FIG. 9 in an open position.
Figure 12:
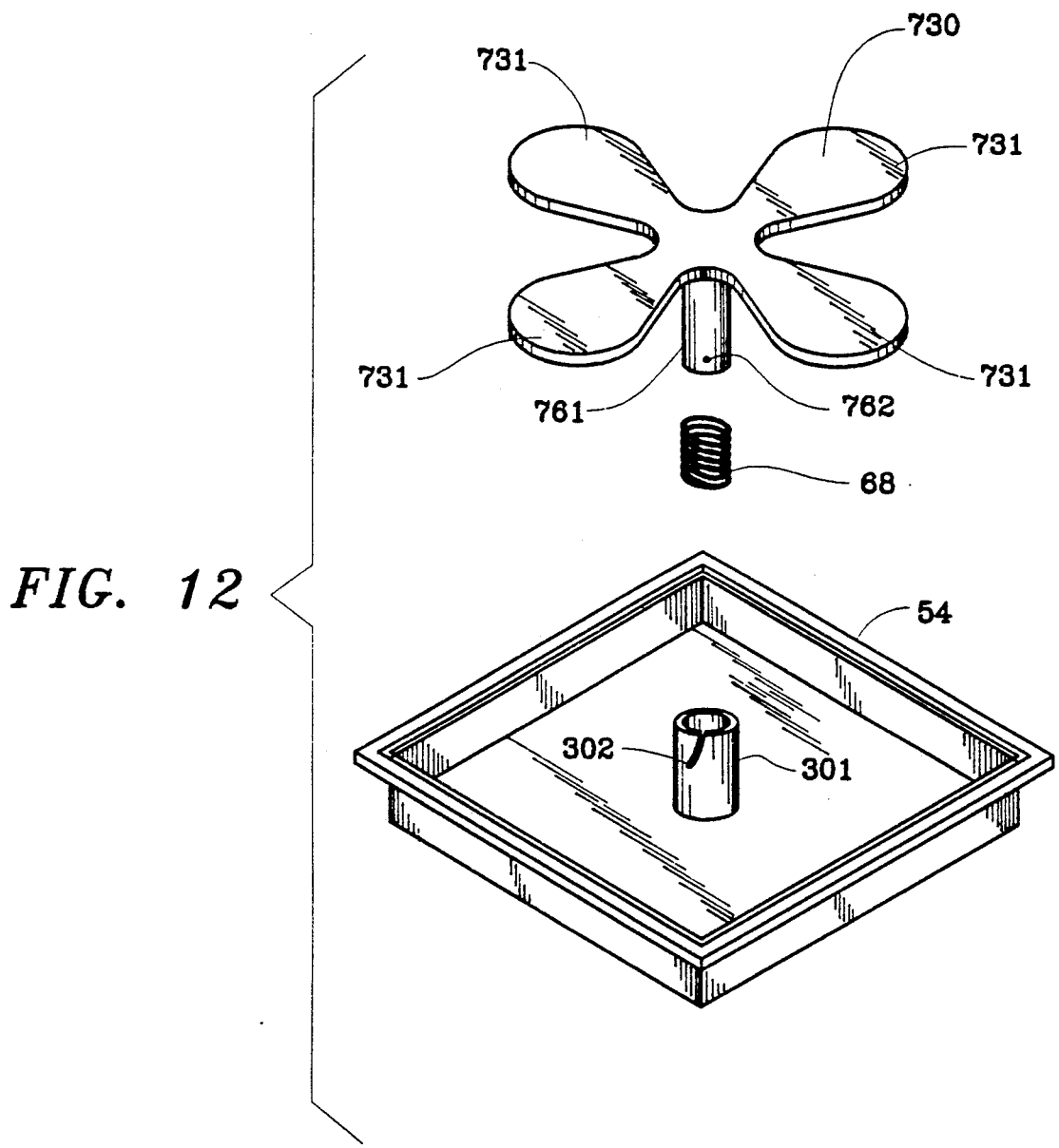
FIG. 12 is an exploded view showing details of a cartridge including the vent sealing structure of FIG. 9.

Referring now to FIGS. 10-12, there is shown an alternate embodiment of the vent sealing apparatus of the inventive cartridge. As shown therein, base member 54 includes a modified cylindrical spring support structure 301, including therein a circumferential slot 302. The cartridge cover is modified as shown at 621 to include a predetermined arrangement of openings 721. A rotatable cover 730 is provided for the openings 721, replacing the diaphragm 66. The cover 730 is provided with a number of individual cover portions 731 mating with the openings 721. Cover 730 includes a rotatable shaft 761 mounted within the modified support structure 301. Shaft 761 includes a key portion 762 for engaging the slot 302. In operation, as the vent seal is vertically displaced, interaction between slot 302 and key 762 will rotate cover 730 so that the individual cover portions 731 move from a closed position, shown in FIG. 10, to an open position, shown in FIG. 11. Partial or full opening or closing of the openings 721 may be attained by varying the degree of vertical displacement of the modified cover 730.

In another embodiment of the invention cartridge, illustrated in FIGS. 14 to 17, cartridge 80 includes a separate push-button vent seal assembly, shown generally at 90.

Figure 15:
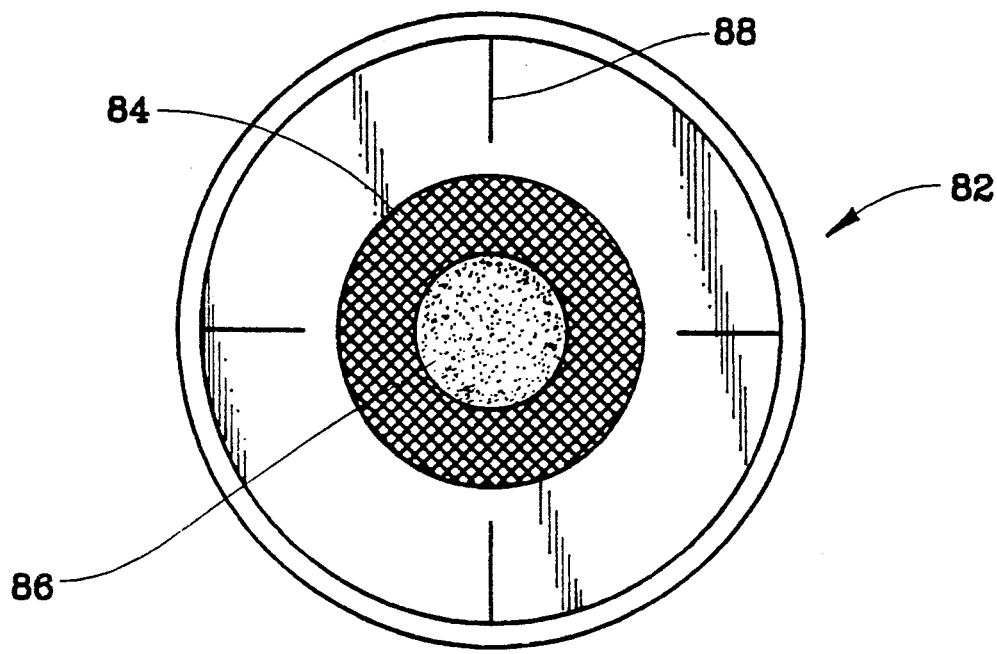
FIG. 15 is a plan view of the cartridge cover shown in FIG. 14.
Figure 14:
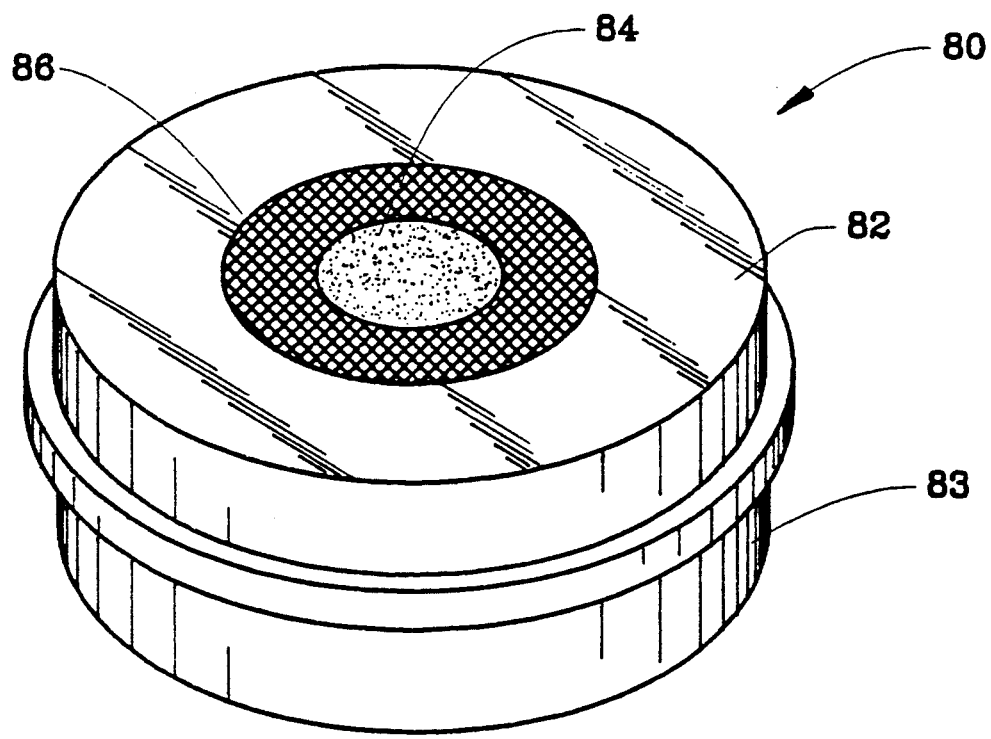
FIG. 14 is a perspective view of another embodiment of a cartridge according to the invention in which a push button mechanism is provided for opening and closing the vent seal mechanism therein.

Access to the push-button 90 is provided through opening 86 in the cartridge cover 82. As seen in FIGS. 14, 15, the opening 86 is centrally located in the top surface of cover 82 and is annularly surrounded by vent openings 84. Referring to FIG. 17, push-button 90 includes cylindrical base member 92 the diameter of which is slightly larger than the diameter of vent opening 84. On the upper surface of base member 92, there is a raised button member 94 the diameter of which coincides with the access opening 86 and, as described below, is aligned therewith. Flange members are provided on the lower periphery of side wall 98 of base member 92 and define openings 97 therebetween, spaced at intervals of 90°. The openings 97 coincide with structural support members 88, also spaced at 90° intervals, located on the underside of cartridge cover 82.

When cartridge cover 82 and cartridge base member 82 are assembled with volatile substance 100 located in lower chamber 85, membrane 56 and support member 64, spring 68 and push-button 90 interposed therebetween, as shown in FIG. 16, support members 88 are aligned with opening 97 and fitted therebetween, such that projecting button member 94 fits within opening 86 and base member 92 and O-ring 70 will be pressed against and block access to (i.e. close) vent openings 84. By pushing down on button member 94 through opening 86 against the action of spring 68, while slightly rotating the push button assembly, flange members 96 will ride down and under structural support members 88 to thereby unblock (i.e. open) vent openings 84 to allow diffusion of volatilized substance through the internal vents 78 and into the ambient surrounding through vent openings 84 (see arrows 99 in FIG. 17).

It will be noted that in this embodiment of the invention, spring 68 is secured directly to the underside of the push-button assembly and the shaft 76 and spring support chamber 86 (in the embodiment described in connection with FIG. 5) may be omitted. In this case, spring 68 rests on solid portion or pedestal 87 centrally located in cartridge base member 83.

From the above description it will be apparent that the push-button vent seal assembly incorporates a mechanism similar to that available for ball point pens to latch the diaphragm (base member 92) alternately in the withdrawn (open) position such as shown in of FIG. 17 and in a closed position as shown in FIG. 16.

Referring now to FIG. 13, there is shown an electrical circuit for controlling the various operations of the device as hereinabove described. Thus, there is shown a connection of a power supply chip IC1, including a peak current limiting resistor R1 and load current limiting capacitor C2 together with a DC filter capacitor C1 to provide a 5 volt DC voltage to the various electronic components of the control circuit. The cartridge control circuit includes the sensing switch 22, shown as S4, which provides 5 V DC to activate the control circuit upon sensing insertion of the cartridge.

When activated, solenoid L1 pulls in the cartridge to position the same over the hot plate, for example. The solenoid is then latched to retain the cartridge properly positioned until ejected. Thermostat T1, normally closed for temperatures below 41° C., causes release of the cartridge when operation is terminated and the cartridge has cooled to 41° C. De-energizing of solenoid L1 causes ejection of the cartridge. The heater control portion of the circuit of FIG. 13 turns the heater H1 on when the cartridge insertion is sensed by switch S4, and turns the heater off upon termination of the dispensing operation. Switch S1 provides the restart switch 42 for a cycle, while switch S2 is the abort switch, or eject switch 40 which may be used to end the cycle. An electronic latch is provided for latching the logic control signal to keep the heater on, and LED D1 is the indicator 44 shown in FIG. 2. Switch S3 is the switch 30 for selecting single or continuous operation.

Timing of the cycles is controlled by two timing circuits, shown as integrated circuit chips IC7 and IC8. Thermostat T2 is used to initiate the timing cycle when the heater temperature reaches 82° C. T2 is a normally open thermostatic switch, which closes when the temperature attains 82° C. Abort switch S2 also ends the timing cycle, which runs on a ten minute cycle having ON times adjustable between one and nine minutes in accordance with the setting of resistor R24, forming the duration control switch 38.

Solenoid L2 is the solenoid 26 of the drawing figures and is used to open and close the cover vents 72. Integrated circuit chips IC9, IC10 and IC11 are triac drivers used to convert the logic signals for the solenoids and heater to 110 V AC, while the solenoids L1 and L2, and heater H1, are actually switched by triacs TR1, TR2 and TR3.

Of course, other temperature values may be used and the temperature range of 41°-82° C. is only an illustrative value used in the presently preferred embodiment of the invention. Similarly, the cycle time of 10 minutes is illustrative and not to be considered as restrictive of the invention.

Since many volatile substances are volatilized at room temperature or when heated by sunlight, since the primary control of dispersal of the substance is in the membrane 56, a manual vent locking device, for example, the push-button vent seal assembly, previously described, may be provided to permit operation of the cartridge independent of any further device. That is, the inventive cartridge structure may be used as an air freshener or volatilizer, independent of any further heating device. Alternatively, for some applications it may be necessary to provide additional heat but not the further secondary flow control afforded by the device structure as hereinabove described. For such applications there may be provided a cartridge including a manual vent locking device, together with a small heater, heat lamp, or hot plate, to provide a simpler molecular diffusion controller than previously described, for example, in connection with FIGS. 1-3.

The foregoing description of the preferred embodiment of the invention has been presented for purposes of illustration and description and is not intended to be exhaustive or to limit the invention to the precise forms disclosed, since many modifications and variations are possible in light of the above teaching. The embodiment was chosen and described in order best to explain the principles of the invention and its practical application, thereby to enable others skilled in the art best to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

I claim:

1. In an apparatus for diffusing a volatilizable substance into an ambient atmosphere, a replaceable cartridge for containing the substance and for providing control of diffusion thereof, comprising:
   a base;
   a membrane means cooperating with said base to form a first chamber for containing the substance for volatilization;
   said membrane means having predetermined characteristics for controlling a dispersal rate for a vaporized form of the substance;
   a cover cooperating with said base for enclosing said membrane means in said cartridge;
   a second chamber formed between said cover and said membrane means for the vaporized substance;
   said cover including vent means for venting the vaporized substance from said second chamber to the ambient atmosphere;
   vent seal means for releasably sealing said vent means to permit controlled passage of the vaporized substance from the cartridge to the ambient atmosphere;
   catalyst means for emitting energy to release said substance from a carrier therefor,
   control means for controlling said catalyst means,
   said control means comprising an electrical control circuit for controlling timing of operation of said vent seal means;
   displacing means for sensing partial insertion of said cartridge into a slot and for positioning said cartridge to receive energy from said catalyst means to effect volatilization of said substance; and
   means for engaging said vent seal means of said cartridge and for controlling operation thereof, thereby providing further control of passage of the vaporized substance from the cartridge to the ambient atmosphere.

2. In an apparatus for diffusing a volatilizable substance into an ambient atmosphere, a replaceable cartridge for containing the substance and for providing control of diffusion thereof, comprising:
   a base;
   a membrane means cooperating with said base to form a first chamber for containing the substance for volatilization, said membrane means comprising a membrane having a porous structure wherein pores of said porous structure are non-uniformly distributed, said pores having a larger diameter being distributed in said membrane closer to a second chamber and said pores having a smaller diameter being distributed in said membrane closer to said first chamber;
   a cover cooperating with said base for enclosing said membrane means in said cartridge;
   said second chamber formed between said cover and said membrane means for the vaporized substance;
   said cover including vent means for venting the vaporized substance from said second chamber to the ambient atmosphere; and
   vent seal means for releasably sealing said vent means to permit controlled passage of the vaporized substance from the cartridge to the ambient atmosphere.

3. In an apparatus for diffusing a volatilizable substance into an ambient atmosphere, a replaceable cartridge for containing the substance and for providing control of diffusion thereof, comprising:
   a base;
   a membrane means cooperating with said base to form a first chamber for containing the substance for volatilization;
   a cover cooperating with said base for enclosing said membrane means in said cartridge;
   a second chamber formed between said cover and said membrane means for the vaporized substance;
   said cover including vent means for venting the vaporized substance from said second chamber to the ambient atmosphere; and
   vent seal means for releasably sealing said vent means to permit controlled passage of the vaporized substance from the cartridge to the ambient atmosphere wherein said vent seal means comprises a diaphragm for closing an opening in said vent means, a sealing ring surrounding said diaphragm for sealing said closed vent means, a spring for biasing said diaphragm against said cover, and a support chamber for supporting said spring.

4. A diffusing apparatus as recited in claim 3 wherein said membrane means has predetermined characteristics for controlling the dispersal rate for a vaporized form of the substance.

5. A diffusing apparatus as recited in claim 3 wherein said membrane means comprises a membrane and a support member therefor.

6. A diffusing apparatus as recited in claim 5 wherein said support member includes port means for passage of the vaporized substance from said first chamber to said second chamber.

7. A diffusing apparatus as recited in claim 3 wherein said membrane means comprises a membrane having a porous structure.

8. A diffusing apparatus as recited in claim 7 wherein pores of said porous structure are substantially uniform in size.

9. A diffusing apparatus as recited in claim 3 wherein said membrane means comprises a semipermeable membrane.

10. A diffusing apparatus as recited in claim 3 wherein said substance comprises an agent to be dispersed and a vehicle for carrying said agent to be dispersed.

11. A diffusing apparatus as recited in claim 3 wherein said support chamber comprises a cylindrical chamber in said first chamber of said cartridge, and further comprising an opening in said membrane means for at least one of said spring and said cylindrical chamber.

12. A diffusing apparatus as recited in claim 4 further comprising compression means for displacing said diaphragm against said bias exerted by said spring to open said vent means thereby permitting controlled passage of the vaporized substance from the cartridge to the ambient atmosphere.

13. In an apparatus for diffusing a volatilizable substance into an ambient atmosphere, a replaceable cartridge for containing the substance and for providing control of diffusion thereof, comprising:
- a base;
- a membrane means cooperating with said base to form a first chamber for containing the substance for volatilization, said membrane means comprising a membrane having a porous structure wherein pores of said porous structure are nonuniformly distributed, said pores having a larger diameter being distributed in said membrane closer to a second chamber and said pores having a smaller diameter being distributed in said membrane closer to said first chamber;
- a cover cooperating with said base for enclosing said membrane means in said cartridge;
- said second chamber formed between said cover and said membrane means for the vaporized substance;
- said cover including vent means for venting the vaporized substance from said second chamber to the ambient atmosphere; and
- vent seal means for releasably sealing said vent means to permit controlled passage of the vaporized substance from the cartridge to the ambient atmosphere, wherein said vent seal means comprises a cylindrical chamber in said first chamber of said cartridge, a biasing spring within said cylindrical chamber, a rotatable cover means, said rotatable cover means including a cover for opening and closing an opening in said vent means and a keyed shaft therefor, said cylindrical chamber including a circumferential slot engaging a key of said keyed shaft thereby to rotate said cover and controllably open and close said opening in said vent means when said shaft is longitudinally displaced in said cylindrical chamber against biasing force exerted by said biasing spring.

14. A diffusing apparatus as recited in claim 13 further comprising compression means for longitudinally displacing said rotatable cover against said biasing force exerted by said spring to open and close said opening in said vent means thereby permitting controlled passage of the vaporized substance from the cartridge to the ambient atmosphere.

15. In an apparatus for diffusing a volatilizable substance into an ambient atmosphere, a replaceable cartridge for containing the substance and for providing control of diffusion thereof, comprising:
- a base;
- a membrane means cooperating with said base to form a first chamber for containing the substance for volatilization, said membrane means comprising a membrane having a porous structure wherein pores of said porous structure are nonuniformly distributed, said pores having a larger diameter being distributed in said membrane closer to a second chamber and said pores having a smaller diameter being distributed in said membrane closer to said first chamber;
- a cover cooperating with said base for enclosing said membrane means in said cartridge;
- said second chamber formed between said cover and said membrane means for the vaporized substance;
- said cover including vent means for venting the vaporized substance from said second chamber to the ambient atmosphere;
- vent seal means for releasably sealing said vent means to permit controlled passage of the vaporized substance from the cartridge to the ambient atmosphere; and
- heater means for heating said cartridge to release said volatilizable substance from a carrier therefor, and control means for controlling said vent seal means comprising an electrical control circuit for controlling timing of operation of said vent seal means.

16. A diffusing apparatus as recited in claim 14 wherein said control means comprises displacing means for sensing partial insertion of said cartridge into a slot and for positioning said cartridge to receive energy from said heater means to effect volatilization of said substance.

17. In an apparatus for diffusing a volatilizable substance into an ambient atmosphere, a replaceable cartridge for containing the substance and for providing control of diffusion thereof, comprising:
- a base;
- a membrane means cooperating with said base to form a first chamber for containing the substance for volatilization, said membrane means comprising a membrane having a porous structure wherein pores of said porous structure are non-uniformly distributed, said pores having a larger diameter being distributed in said membrane closer to a second chamber and said pores having a smaller diameter being distributed in said membrane closer to said first chamber;
- a cover cooperating with said base for enclosing said membrane means in said cartridge;
- said second chamber formed between said cover and said membrane means for the vaporized substance;
- said cover including vent means for venting the vaporized substance from said second chamber to the ambient atmosphere;
- vent seal means for releasably sealing said vent means to permit controlled passage of the vaporized substance from the cartridge to the ambient atmosphere;
- catalyst means for emitting energy to release said substance from a carrier therefor; and
- control means for controlling said catalyst means, wherein said control means further comprises means for engaging said vent seal means of said cartridge and for controlling operation thereof, thereby providing further control of passage of the vaporized substance from the cartridge to the ambient atmosphere.

* * * * *